US012758664B2

(12) United States Patent
Wu et al.

(10) Patent No.: US 12,758,664 B2
(45) Date of Patent: Oct. 13, 2026

(54) SYSTEMS AND METHODS FOR FLUID OR STRUCTURE SURFACE DISINFECTION USING DEEP UV PICOSECOND LASER

(71) Applicant: Gauss Lasers Tech (Shanghai) Co., Ltd., Shanghai (CN)

(72) Inventors: Ming Wu, Shanghai (CN); Hongyan Ren, Shanghai (CN); Shiyun Zhou, Shanghai (CN); Yuxin Leng, Shanghai (CN); Zhiwen Liu, Shanghai (CN); Jiashun Liu, Shanghai (CN); Tingxia Li, Shanghai (CN); Yiming Cai, Shanghai (CN); Tongxin Li, Shanghai (CN); Shian Zhou, Shanghai (CN)

(73) Assignee: GAUSS LASERS TECH (SHANGHAI) CO., LTD., Shanghai (CN)

( * ) Notice: Subject to any disclaimer, the term of this patent is extended or adjusted under 35 U.S.C. 154(b) by 853 days.

(21) Appl. No.: 17/879,028

(22) Filed: Aug. 2, 2022

(65) Prior Publication Data

US 2023/0173115 A1 Jun. 8, 2023

Related U.S. Application Data

(63) Continuation of application No. PCT/CN2021/136219, filed on Dec. 8, 2021.

(51) Int. Cl.
*A61L 2/10* (2026.01)
*A61L 2/24* (2006.01)

(52) U.S. Cl.
CPC .................. *A61L 2/10* (2013.01); *A61L 2/24* (2013.01); *A61L 2202/11* (2013.01); *A61L 2202/14* (2013.01)

(58) Field of Classification Search
CPC .................................... A61L 2/08; A61L 9/18
See application file for complete search history.

(56) References Cited

U.S. PATENT DOCUMENTS

| | | | | |
|---|---|---|---|---|
| 10,850,115 B2 * | 12/2020 | Zhou | A61N 5/0616 | |
| 2013/0244449 A1 * | 9/2013 | Baird | B23K 26/0624 438/795 | |

(Continued)

FOREIGN PATENT DOCUMENTS

| | | |
|---|---|---|
| CN | 104415464 A | 3/2015 |
| CN | 212347217 U | 1/2021 |

(Continued)

OTHER PUBLICATIONS

International Search Report and Written Opinion in related PCT Application No. PCT/CN2021/136219 dated Aug. 26, 2022 (8 pages).

*Primary Examiner* — Donald R Spamer
*Assistant Examiner* — Kayla Rose Sarantakos
(74) *Attorney, Agent, or Firm* — Bayes PLLC

(57) ABSTRACT

Embodiments of systems and methods for fluid or structure surface disinfection using a series of pulsed lasers are disclosed. In an example, a system for fluid or structure surface disinfection includes a laser source, an optical module, and a controller coupled to the optical module. The laser source is configured to generate a laser stream. The optical module is configured to shape the laser stream and direct the laser stream toward a portion of a surface of a structure. The controller is coupled to the optical module and configured to control the optical module to direct the laser stream toward the portion of the surface of the structure.

18 Claims, 9 Drawing Sheets

100

(56) References Cited

U.S. PATENT DOCUMENTS

| | | | | |
|---|---|---|---|---|
| 2013/0248734 | A1 * | 9/2013 | Berry | A61L 9/18 250/435 |
| 2018/0071416 | A1 | 3/2018 | Toboada et al. | |
| 2021/0206664 | A1 * | 7/2021 | Bilenko | A47L 7/0061 |
| 2023/0165995 | A1 * | 6/2023 | Zacchigna | A61L 9/18 250/435 |

FOREIGN PATENT DOCUMENTS

| | | | | |
|---|---|---|---|---|
| CN | 113251554 | A | 8/2021 | |
| CN | 113663094 | A | 11/2021 | |
| KR | 102320500 | B1 * | 11/2021 | B23K 26/361 |

* cited by examiner

100

300

500

620

700

SYSTEMS AND METHODS FOR FLUID OR STRUCTURE SURFACE DISINFECTION USING DEEP UV PICOSECOND LASER

CROSS REFERENCE TO RELATED APPLICATION

This application is a continuation of International Application No. PCT/CN2021/136219, filed on Dec. 8, 2021, which is hereby incorporated by reference in its entirety.

BACKGROUND

Embodiments of the present disclosure relate to systems and methods for fluid or structure surface disinfection using lasers.

The outbreak of the pandemic COVID-19 calls for every potential tool, including light treatment, to disinfect fluid (such as air) or structure surface (such as groceries or other consumer products and the respective packages) to prevent the spread of the virus and reduce the impact of the pandemic. It is well known that high-intensity ultraviolet (UV) light has germicidal properties that may be used to disinfect a fluid or structure surface of objects. However, the UV lamps currently used for disinfection are only applicable to limited types of viruses and only for small areas. In addition, the time required for disinfection by such UV lamps is also long.

Therefore, there is a need for a new disinfection device that can kill most types of viruses for a large area in a short period of time.

SUMMARY

Embodiments of systems and methods for fluid or structure surface disinfection using picosecond deep UV laser are disclosed herein.

In one example, a system for fluid or structure surface disinfection includes a laser source, an optical module, and a controller coupled to the laser source and the optical module. The laser source is configured to generate a laser stream. The optical module is configured to shape the laser stream and direct the laser stream toward a portion of a surface of a structure. The controller is coupled to the optical module and configured to control the optical module to direct the laser stream toward the portion of the surface of the structure.

In another example, a method for fluid or structure surface disinfection is disclosed. A laser stream is generated by a laser source. The generated laser stream is then formed into a predefined shape. The shaped laser stream is then directed toward a portion of a surface of a structure.

BRIEF DESCRIPTION OF THE DRAWINGS

The accompanying drawings, which are incorporated herein and form a part of the specification, illustrate embodiments of the present disclosure and, together with the description, further serve to explain the principles of the present disclosure and to enable a person skilled in the pertinent art to make and use the present disclosure.

Figure 1:
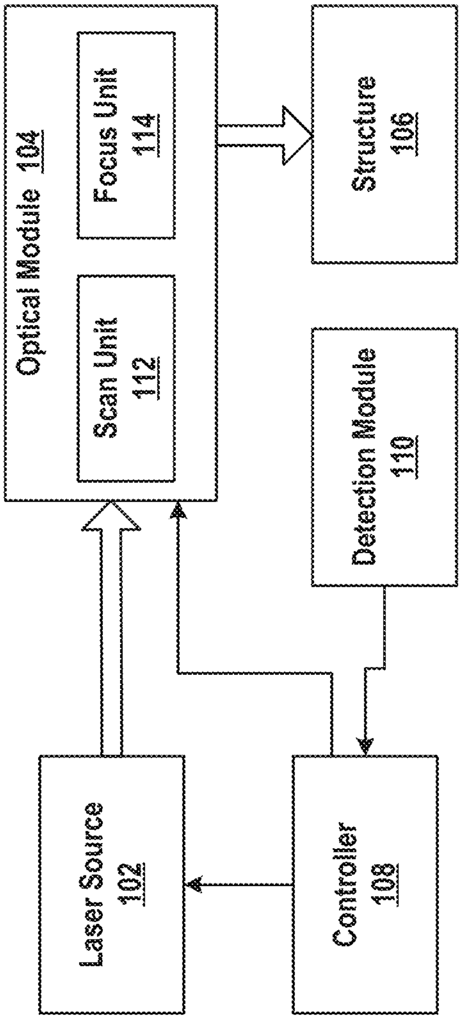
FIG. 1 illustrates a schematic diagram of an exemplary system for fluid or structure surface disinfection using picosecond deep UV laser, according to some embodiments of the present disclosure.

Embodiments of the present disclosure will be described with reference to the accompanying drawings.

DETAILED DESCRIPTION

Although specific configurations and arrangements are discussed, this should be understood as being for illustrative purposes only. A person skilled in the pertinent art will recognize that other configurations and arrangements may be used without departing from the spirit and scope of the present disclosure. It will be apparent to a person skilled in the pertinent art that the present disclosure may also be employed in a variety of other applications.

It is noted that references in the specification to "one embodiment," "an embodiment," "an example embodiment," "some embodiments," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of a person skilled in the pertinent art to affect such feature, structure or characteristic in connection with other embodiments whether or not explicitly described.

In general, terminology may be understood at least in part from usage in context. For example, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Existing systems using light treatment to disinfect fluid or structure surfaces have certain drawbacks. For instance, the UV lamps used for disinfection in these systems are only applicable to limited types of viruses and only for small areas. In addition, the time required for disinfection by such UV lamps is also long. In view of the recent outbreak of COVID 19, an effective disinfection treatment approach to kill most types of viruses, including different species of COVID 19 viruses, is needed.

In some embodiments, pulsed UV lasers may directly cause irreversible damage to DNA/RNA. Specifically, due to the high peak power (e.g., 20 MW) in a very short period of time (e.g., picoseconds), when acting on viruses or other pathogens, pulsed UV lasers may excite viral (or other pathogens) molecules, even for deep UV (DUV) light. In some embodiments, the concentration of the excited molecules may be much higher than that of the excited molecules obtained with low peak power UV light. This instantaneous transfer of energy may affect the dynamics of the resulting system and promote radical reactions, resulting in irreversible (irrecoverable) damage to viral DNA/RNA. This damage may be too fast to be repaired through photoactivation-mediated or other DNA/RNA repair mechanisms. Accordingly, the replication and propagation of the virus may be ultimately prevented.

Figure 7:
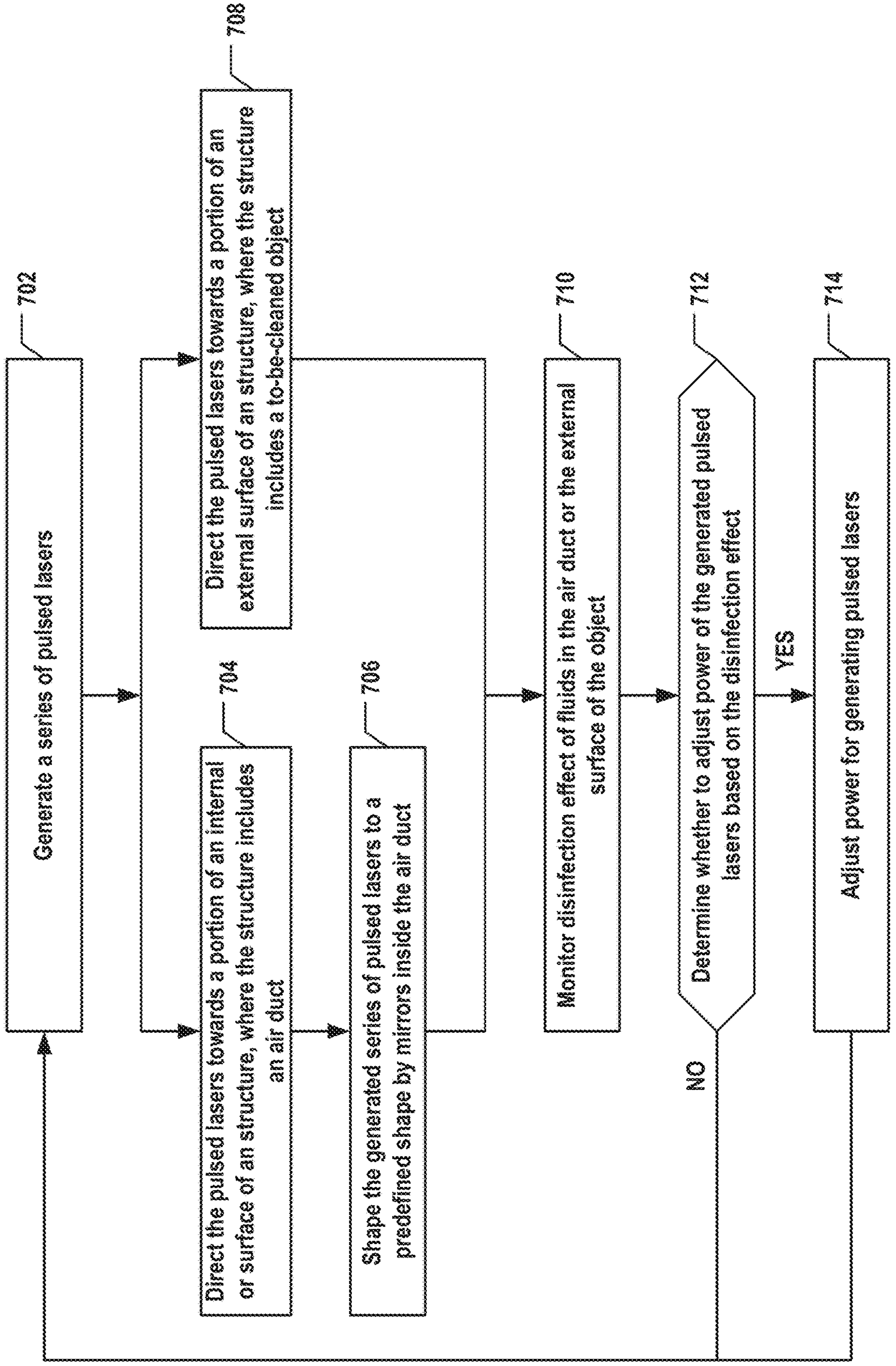
FIG. 7 is a flowchart of an exemplary method for fluid or structure surface disinfection using picosecond deep UV laser, according to some embodiments.

FIG. 7 Various embodiments in accordance with the present disclosure provide systems and methods for fluid or structure surface disinfection using picosecond DUV laser. By using picosecond DUV lasers for disinfection, most types of viruses can be quickly killed, due to the damage to viral DNA/RNA caused by the energy transfer from the DUV light. The shorter the wavelength of DUV used, the more obvious the virus-killing effect is due to the damage to the viral DNA/RNA caused by the DUV light. In addition, the disclosed systems and methods provide an effective approach to kill a large variety of viruses by forming a DUV screen in a circulating system. This allows the virus-killing effect of the DUV to be applicable to a large amount of air or other fluid systems, thereby increasing the applicable areas of DUV lights in viral disinfection. Further, by directing DUV to different solid structure surfaces through UV light-guiding arms or other optical fibers or optical cables, the disclosed DUV disinfection methods and systems may be applied to many different systems and environments, further promoting its applications in different areas of viral disinfection including in COVID 19 virus prevention and disinfection.

FIG. 1 illustrates a schematic diagram of an exemplary disinfection system 100 for fluid or structure surface disinfection using picosecond DUV laser, according to some embodiments of the disclosure. As illustrated, disinfection system 100 may include a laser source 102, an optical module 104, a structure 106, and a controller 108. Laser source 102 may be any suitable type of laser source including, but not limited to, fiber lasers, solid-state lasers, gas lasers, and semiconductor lasers. Laser source 102 may be configured to generate a series of pulsed lasers at any suitable wavelengths, such as 200 nm, 250 nm, 280 nm, 300 nm, 532 nm laser, 600-1,000 nm lasers, 1,064 nm laser, 1,550 nm laser, etc. In some embodiments, a laser at a DUV region with a wavelength range between 200 nm and 300 nm may be used.

In some embodiments, the duration of each pulsed laser is not greater than a certain value (e.g., 50 picoseconds, 100 picoseconds). In some embodiments, the duration of each pulsed laser may be between 50 femtoseconds (fs) and 50 picoseconds (ps), such as 50 fs, 60 fs, 70 fs, 80 fs, 90 fs, 100 fs, 200 fs, 300 fs, 400 fs, 500 fs, 600 fs, 600 fs, 800 fs, 900 fs, 1 ps, 2 ps, 3 ps, 4 ps, 5 ps, 6 ps, 7 ps, 8 ps, 9 ps, 10 ps, 20 ps, 30 ps, 40 ps, 50 ps, in any range bounded by the lower end by any of these values, or in any range defined by any two of these values. In some embodiments, other ranges of a pulsed laser may also be possible and contemplated. For instance, the duration of each pulsed laser may be between 100 fs and 100 ps, 1 ps and 50 ps, 1 ps and 100 ps, etc.

Figure 3:
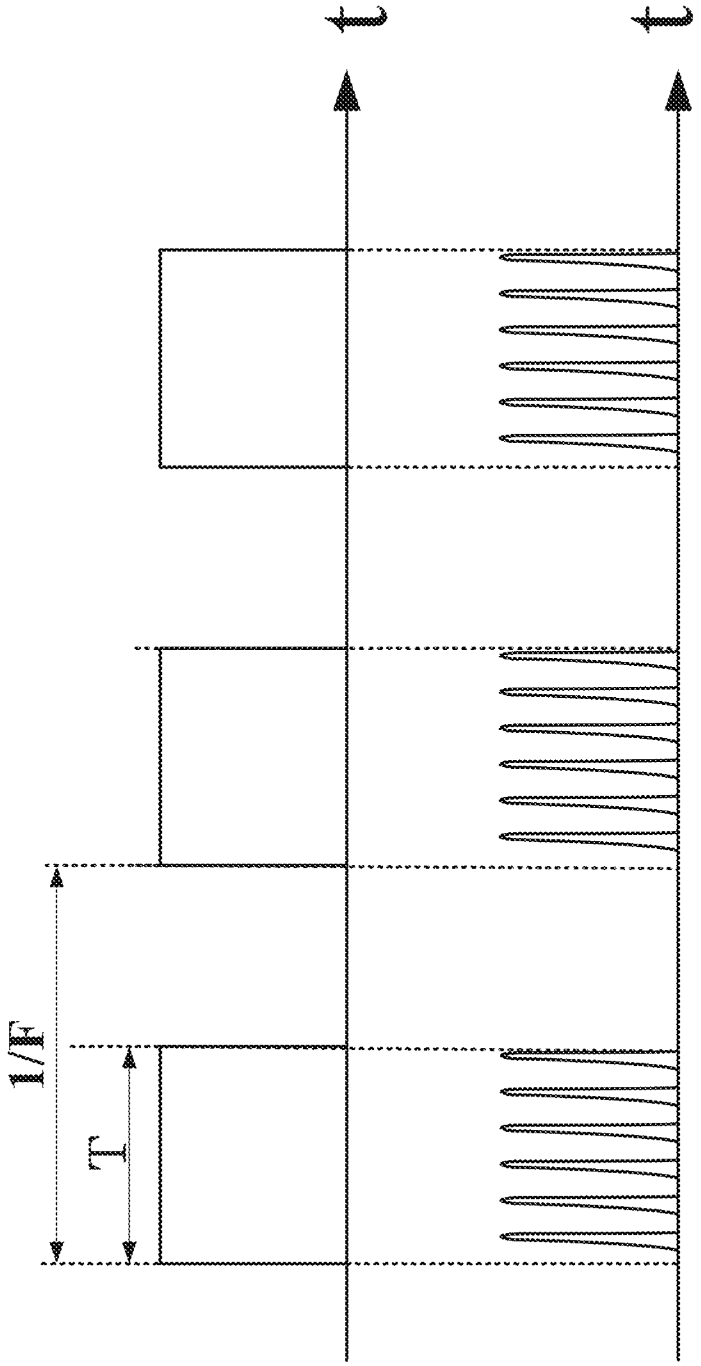
FIG. 3 illustrates exemplary pulsed lasers having a series of bursts, according to some embodiments of the present disclosure.

Each pulsed laser may be a single pulse or include a series of bursts. FIG. 3 illustrates exemplary pulsed lasers having a series of bursts, according to some embodiments of the present disclosure. The series of pulsed lasers may be generated by a laser source at a frequency F, and the pulse width of each pulsed laser is T. When the pulsed lasers are generated in burst mode, N bursts may be generated in the same pulse width T, where N is an integer greater than 1, such as between 2 and 100. In some embodiments, the frequency of the bursts is in the scale of nanosecond (ns), and the frequency F of the laser pulses is in the scale of microsecond (μs). As a result, the laser energy may be first accumulated by the bursts within each pulse in the scale of ns and then accumulated by the pulses in the scale of ps, thereby achieving a very high energy density (i.e., laser power) without the need of increasing the peak energy. That is, each focused laser spot may be formed by 1-N burst.

Referring back to FIG. 1, in some embodiments, the pulsed lasers generated by laser source 102 may have a single wavelength or a plurality of wavelengths, such as two or three different wavelengths. Pulsed lasers having different wavelengths may be separately, simultaneously, or alternatingly generated. In some embodiments, the wavelength of the pulsed lasers generated by laser source 102 is between 100 nm and 300 nm, such as 200 nm, 220 nm, 240 nm, 260 nm, or 280 nm. In some embodiments, the output frequency of laser source 102 is between 20 kHz and 1,000 kHz. In some embodiments, the average output power of laser source 102 is between 1 W and 100 W. It is to be noted that the parameters of pulsed lasers and laser source 102 disclosed above are for illustrative purposes only, and can be other proper values.

Optical module 104 may be optically coupled to laser source 102 and include a scan unit 112 and a focus unit 114. Optical module 104 may be configured to provide a series of focused laser spots on a structure (e.g., a mirror inside an air duct or an object surface) based on the series of pulsed lasers generated by laser source 102. In some embodiments, optical module 104 may be operatively coupled to controller 108 and receive control signals and instructions from controller 108, so as to generate lasers with different properties (e.g., different laser power, different laser wavelengths, etc.) Scan unit 112 may be configured to, based on the control of controller 108, change directions in which at least some of the pulsed lasers emit towards a structure's surface. That is, scan unit 112 may scan the pulsed lasers within a predefined scan angle at a predefined scan rate, as controlled by controller 108, toward structure 106. For instance, scan unit 112 may scan the pulsed lasers at a scan angle such that the pulsed lasers are not incident on a structure surface perpendicularly. In some embodiments, scan unit 112 includes a galvanometer and/or a polarizer. Scan unit 112 may further include any other suitable scanning mirrors and scanning refractive optics.

Focus unit 114 may be configured to focus each of the pulsed lasers to form a series of focused laser spots when reaching a structure surface. In some embodiments, a dimension of each of the focused laser spots is between 1 micrometer (μm) and 500 μm, such as 1 μm, 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm, 200 μm, 300 μm, 400 μm, 500 μm, in any range bounded by the lower end by any of these values, or in any range defined by any two of these values. The shape of each focused laser spot may include, for example, round, rectangle, square, irregular, or any suitable shapes. In some embodiments, each focused laser spot has a substantially round shape with a diameter between 1 μm and 300 μm. It is to be noted that the dimensions of a series of focused laser spots may be substantially the same or different. By focusing the beams of pulsed lasers onto focused laser spots, the energy density may be significantly increased.

Structure 106 may be in different shapes and sizes. In some embodiments, structure 106 may include an external structure or an internal structure. For instance, when using an air duct for air or other fluid disinfection, structure 106 may refer to an internal structure, e.g., an internal wall of an air duct. In these embodiments, when the pulsed lasers are directed towards structure 106, the pulsed lasers are directed towards an internal structure (e.g., the internal wall of an air duct). In some embodiments, structure 106 may refer to an external structure, e.g., an external surface of an object. In these embodiments, when the pulsed lasers are directed towards structure 106, the pulsed lasers are actually directed towards the external surface of an object.

Controller 108 may be operatively coupled to laser source 102 and/or optical module 104, and control the operations of laser source 102 and/or optical module 104 via control signals and instructions. In some embodiments, controller 108 may be configured to control laser source 102 to generate lasers with different properties, such as different spot shapes or sizes, different laser powers of laser spots, different wavelengths, or different burst types, etc. In some embodiments, controller 108 may be configured to control optical module 104 to direct the series of focused laser spots towards different areas of an object's surface according to a predefined pattern or according to a shape or structure of a detected object during the disinfection, or direct the series of focused laser spots at different angles towards an internal wall of an air duct. Further factors that can be controlled by controller 108 include, but are not limited to, the scanning path, scanning speed, scanning area size, etc.

As shown in FIG. 1, in some embodiments, disinfection system 100 may further include a detection module 110 configured to detect the shape and size of a to-be-disinfected target object and provide detection data to controller 108. For instance, for a structure surface disinfection system 100, a detection module 110 may be included in the system. Detection module 110 may include, but is not limited to, a camera, a sensor, a thermal imaging machine, an x-ray machine, an ultrasound machine, or a detection device of any other suitable structure or shape. It is to be noted that detection module 110 may be part of disinfection system 100 or a standalone device separate from disinfection system 100. For example, detection module 110 may be a dedicated imaging device that takes images of a target object and transmits the images, or any detection data derived from the images, to controller 108. It is further understood that the detection of a target object may be carried out based on any suitable modalities, such as images, videos, sounds, texts, etc. In addition to obtaining initial detection data based on the initial detection of a target object, in some embodiments, detection module 110 may perform the detection continuously during a disinfection process or upon request by a human operator who monitors the status of the disinfection. For instance, detection module 110 may further detect a scan pattern formed on a target object.

Figure 2:
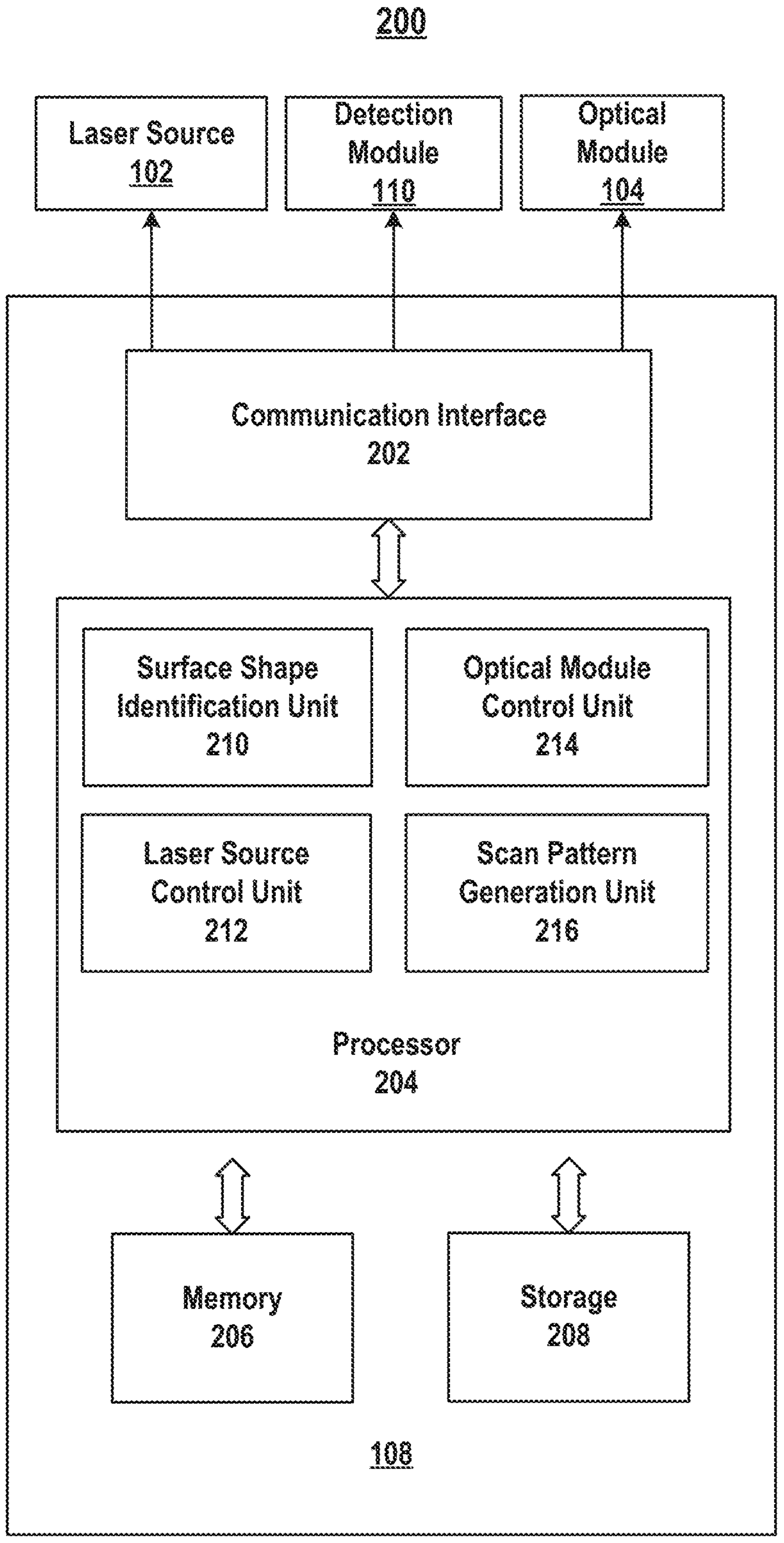
FIG. 2 illustrates a schematic diagram of an exemplary controller, according to some embodiments of the present disclosure.

FIG. 2 illustrates a schematic diagram of exemplary controller 108, according to some embodiments of the disclosure. Controller 108 may control operations of laser source 102 and/or optical module 104, for example, to generate, shape, adjust, and move a series of focused laser spots on structure 106, and/or to form a scan pattern based on a detection of the surface structure of a target object. In some embodiments, controller 108 may receive detection data indicative of the shape and size of the external surface of the target object and provide control instruction indicative of the scan pattern based on the detection data to laser source 102 and/or optical module 104. In some embodiments, controller 108 may control laser source 102 and optical module 104 to operate in a predefined manner. For instance, controller 108 may control laser source 102 to emit pulsed lasers with a predefined shape, size, power, wavelength, burst type, etc. For another instance, controller 108 may control optical module 104 to allow pulsed lasers to be directed towards an internal wall of an air duct at a predefined pattern (e.g., horizontally scan at a predefined incident angle). In some embodiments, controller 108 may dynamically control laser source 102 and optical module 104 based on the instant operation during a disinfection process. For instance, controller 108 may dynamically control laser source 102 to adjust laser power based on the disinfection effect. For another instance, controller 108 may also dynamically control optical module 104 to direct pulsed lasers towards different areas of an object surface based on the instantly obtained external structure information of the object under disinfection.

As illustrated in FIG. 2, controller 108 may include a communication interface 202, a processor 204, a memory 206, and a storage 208. In some embodiments, controller 108 may have different modules in a single device, such as an integrated circuit (IC) chip (implemented as an application-specific integrated circuit (ASIC) or a field-programmable gate array (FPGA), or separate devices with dedicated functions. One or more components of controller 108 may be located along with laser source 102 and/or optical module 104 as part of disinfection system 100 or may be alternatively in a standalone computing device, in the cloud, or another remote location. Components of controller 108 may be in an integrated device or distributed at different locations but communicate with each other through a network (not shown). For example, processor 204 may be a processor on-board laser source 102 and/or optical module 104, a processor inside a standalone computing device, or a cloud processor, or any combinations thereof.

Communication interface 202 may transmit data to and receive data from components such as laser source 102, optical module 104, or detection module 110 via communication cables, a Wireless Local Area Network (WLAN), a Wide Area Network (WAN), wireless networks such as radio waves, a nationwide cellular network, and/or a local wireless network (e.g., Bluetooth™ or WiFi), or other communication methods. In some embodiments, communication interface 202 may be an integrated services digital network (ISDN) card, cable modem, satellite modem, or a modem to provide a data communication connection. As another example, communication interface 202 may be a local area network (LAN) card to provide a data communication connection to a compatible LAN. Wireless links may also be implemented by communication interface 202. In such an implementation, communication interface 202 may transmit and receive electrical, electromagnetic or optical signals that carry digital data streams representing various types of information via a network.

Processor 204 may include any appropriate type of general-purpose or special-purpose microprocessor, digital signal processor, or microcontroller. Processor 204 may be configured as a separate processor module dedicated to controlling laser source 102, optical module 104, and/or detection module 110. Alternatively, processor 204 may be configured as a shared processor module for performing other functions unrelated to controlling laser source 102, optical module 104, and/or detection module 110.

As shown in FIG. 2, processor 204 may include multiple modules, such as a surface shape identification unit 210, a laser source control unit 212, an optical module control unit 214, a scan pattern generation unit 216, and the like. These modules or units (and any corresponding sub-modules or sub-units) may be hardware units (e.g., portions of an integrated circuit) of processor 204 designed for use with other components or to execute a part of a program. The program may be stored on a computer-readable medium, and when executed by processor 204, perform one or more functions. Although FIG. 2 shows units 210-216 all within one processor 204, it is contemplated that these units may be distributed among multiple processors located near, or remotely from, each other.

Surface shape identification unit 210 may be configured to determine the surface shape and size of a target object based on detection data received from detection module 110. The detection data may be indicative of a texture, a shape, a color, and/or size, or any other suitable information associated with the target object under disinfection. For example, any suitable image processing algorithms may be implemented by surface shape identification unit 210 to analyze the images of the target object and derive detection data from the analysis results in the forms of images, videos, sounds, texts, or metadata. In some embodiments, the image processing algorithms may include pattern recognition algorithms that may automatically retrieve feature information of the target object, such as texture, shape, color, and size, using machine learning based on training data.

In some embodiments, based on the surface shape and texture of a target object, scan pattern generation unit 216 may generate a scan pattern for the target object to be disinfected by a series of focused laser spots. Specifically, scan pattern generation unit 216 may determine the size and/or shape of the scan pattern and the parameters of the series of focused laser spots that may form the scan pattern with the desired size and/or shape. For example, the parameters of the series of focused laser spots include, but are not limited to, the path, speed, and/or repetition of the movement of the series of laser spots, size(s) of the laser spots, offset(s) of adjacent laser spots, the density of the laser spots, the repetitiveness of the laser spots, frequency of the laser spots, or any other parameters that may affect the size and/or shape of the scan pattern to be formed by the series of focused laser spots or the power applied by the focused laser spots on the target object during a disinfection process. For instance, an object with high water content may be disinfected using lasers with different laser powers from an object with low water content. For another instance, a regularly shaped object may be scanned using a different scan pattern than an irregularly shaped object.

In some embodiments, in addition to determining the initial scan pattern based on the external surface shape, texture, and size of the target object, scan pattern generation unit 216 may adaptively adjust the scan pattern in real time during a disinfection process. As described above, the update of detection data may be continuously, or upon request, fed into scan pattern generation unit 216, during a disinfection process, by detection module 110. The updated detection data may indicate the progress and status of a disinfection process as well as the surface shape and texture of the target object during the disinfection process. Scan pattern generation unit 216 may thus adaptively adjust the parameters associated with the focused laser spots based on the current progress and the status of the scan pattern and the target object as reflected by the updated detection data. The subsequently focused laser spots may either follow the parameters associated with the initial scan pattern or be adjusted to follow the updated parameters. For example, the size and/or shape of the initial scan pattern may be adjusted to form an updated scan pattern. In another example, the path of movement of the subsequently focused laser spots may be adjusted to form an updated scan pattern in response to an irregular shape and/or texture detected by detection module 110.

It is to be noted that in forming the scan patterns, the series of focused laser spots may be substantially overlapped (e.g., greater than 50% of the number of focused laser spots forming the pattern are overlapped), partially overlapped (e.g., equal to less than 50% of the number of focused laser spots forming the pattern are overlapped), or not overlapped at all. The degree of overlapping between two or more adjacent focused laser spots may vary between 0 and 100% as well, and may correlate with the texture of an object. For instance, instead of adjusting the laser power, an area that requires more intense light treatment may be achieved by just overlapping the focused laser spots.

In some embodiments, laser source control unit 212 may be configured to provide a control instruction to laser source 102 indicative of the initial scan pattern or an updated scan pattern. The control instruction may cause laser source 102 to initialize or adjust various parameters associated with the series of pulsed lasers based on the determined initial scan pattern or updated scan pattern prior to and during a disinfection process, respectively. In some embodiments, the power of laser source 102 is controlled by laser source control unit 212, to affect the size and shape of the focused laser spots or the power applied by the focused laser spots on the surface of a target object. In some embodiments, the number of bursts in each of the pulsed lasers generated by laser source 102 is controlled by laser source control unit 212 to affect the size and shape of the focused laser spots or the power applied by the focused laser spots on the target object. In some embodiments, the frequency of laser source 102 is controlled by laser source control unit 212 to affect the frequency and/or offset of the focused laser spots.

Optical module control unit 214 may be configured to provide a control instruction to optical module 104 indicative of the initial scan pattern or the updated scan pattern. The control instruction may cause optical module 104 to initialize and adjust various parameters associated with the series of pulsed laser spots based on the determined initial scan pattern or updated scan pattern prior to and during a disinfection process, respectively. In some embodiments, scan unit 112 is controlled by optical module control unit 214 to affect the path, direction, speed, and/or repetition of movement of the focused laser spots, which may in turn affect the power of the focused laser spots applied on a target object. In some embodiments, focus unit 114 is controlled by optical module control unit 214 to affect the size and/or shape of the focused laser spots, which may in turn affect the power of the focused laser spots applied on the target object.

Memory 206 and storage 208 may include any appropriate type of mass storage provided to store any type of information that processor 204 may require or generate during a disinfection process. Memory 206 and storage 208 may be a volatile or non-volatile, magnetic, semiconductor, tape, optical, removable, non-removable, or other types of storage device or tangible (i.e., non-transitory) computer-readable medium including, but not limited to, a ROM, a flash memory, a dynamic RAM, and a static RAM. Memory 206 and/or storage 208 may be configured to store one or more computer programs that may be executed by processor 204 to perform functions of laser source 102, optical module 104, and detection module 110 disclosed herein. For example, memory 206 and/or storage 208 may be configured to store program(s) that may be executed by processor 204 to control operations of laser source 102, optical module 104, and detection module 110, and process the data to generate control instructions and any other control signals.

Memory 206 and/or storage 208 may be further configured to store information and data used by processor 204. For instance, memory 206 and/or storage 208 may be configured to store the detection data indicative of the target object surface structure provided by detection module 110. The various types of data may be stored permanently, removed periodically, or disregarded immediately after each detection and/or scan.

It is to be noted that the foregoing described modules or units in FIGS. 1 and 2 may not necessarily be included in each fluid or structure surface disinfection system 100. For instance, the above-described surface shape identification unit 210 and detection module 110 may not be in a fluid disinfection system but be included in a structure surface disinfection system. In a fluid disinfection system, there may be no need to detect the shape and size of the internal structure (e.g., interval wall), since the internal structure of an air duct may be known in advance and remain unchanged during a disinfection process. On the other hand, in a structure surface disinfection system, since different objects may be disinfected in actual disinfection processes, a surface shape identification unit 210 and/or a surface shape identification unit 210 may be used for a disinfection process. Different configurations of fluid or structure surface disinfection systems will be described in more detail in FIGS. 4A-6C.

Figure 4A:
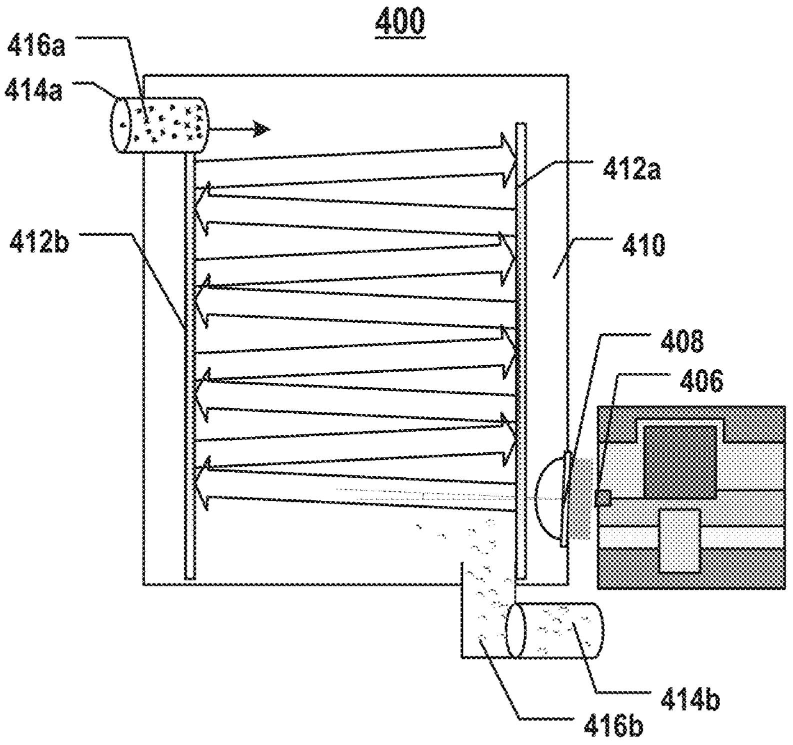
FIGS. 4A-4B illustrate various exemplary air ducts for fluid disinfection, according to various embodiments of the present disclosure.
Figure 4B:
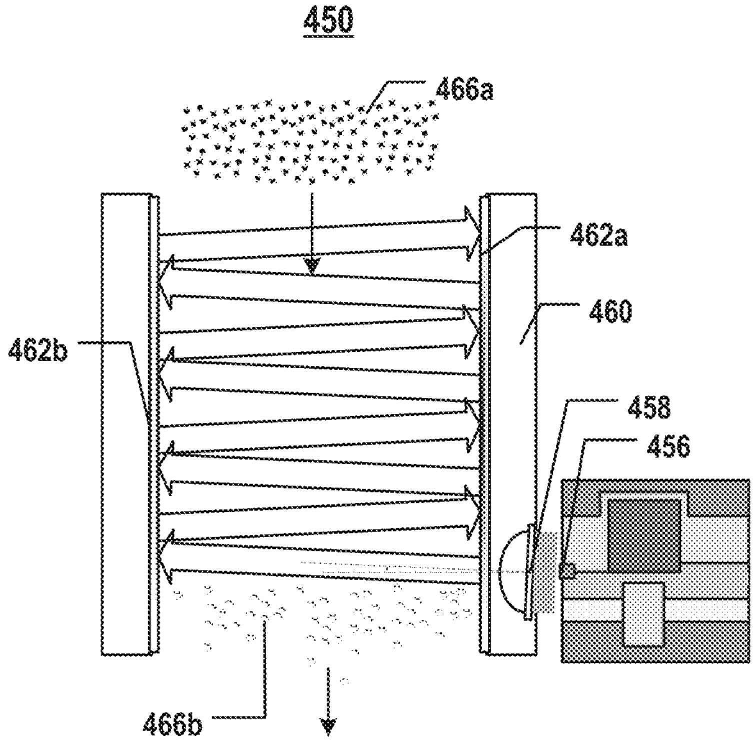

FIGS. 4A and 4B illustrate schematic diagrams of exemplary fluid disinfection systems 400 and 450, according to some embodiments of the present disclosure. In FIG. 4A, fluid disinfection system 400 has closed ends on the top and bottom of an air duct 410. An air inlet 414*a* is disposed on the top left side of the air duct, while an air outlet 414*b* is disposed on the bottom right side of the air duct. Apparently, other ways of disposing an air inlet and air outlet are also possible and contemplated. In some embodiments, air inlet 414*a* and air outlet 414*b* together may serve as a forced-air channel, so that air or other fluids from any source may be guided into the disinfection system 400 for disinfection. On the other hand, in FIG. 4B, fluid disinfection system 450 has open ends on two sides, and thus may be a part of an air circulation system installed inside a facility. In some embodiments, each fluid disinfection system 400 or 450 may further include a laser module that includes a laser emitter 406 or 456, one or more optics 408 or 458, as illustrated in FIGS. 4A and 4B.

Laser emitter 406 or 456 may emit an optical signal at a certain wavelength. For instance, laser emitter 406 or 456 may emit DUV picosecond lasers with a wavelength in the range of 200-300 nm. In some embodiments, laser emitter 406 or 456 may use mode-locking technology to obtain a picosecond seed source, to allow to achieve around 1 um high-power picosecond laser output through optical fiber or solid-state amplification technology, and then use frequency conversion technology to achieve deep ultraviolet wavelengths such as 266 nm to obtain deep ultraviolet picosecond lasers. In some embodiments, through control software, the laser power, frequency and other parameters may be further controlled, and the internal parameters and status may be further monitored. It is to be noted that the aforementioned technologies for emitting DUV picosecond lasers are merely for illustrative purposes but not for limitation. Other techniques for emitting DUV picosecond lasers are also possible and may be applied to laser emitter 406 or 456.

Optics 408 or 458 may include lens, mirrors, or other components that shape the light source to desired shapes (e.g., collimated shape, diverged shape, or any patterned shape). In one embodiment, optics 408 or 458 may include a fast axis collimator (FAC) and a slow axis collimator (SAC), according to one example. In some embodiments, optics 408 and 458 may have functions similar to those described for optical module 104. In some embodiments, fluid disinfection system 400 or 450 may further include a scanner that may direct pulsed lasers towards different directions in a disinfection process. For instance, the scanner may scan a part of an internal wall of an air duct, as further described below, in a 1D or 2D scanning manner by continuously changing horizontal and/or vertical directions. For instance, the scanner may direct the pulsed lasers towards the internal wall of the air duct at a certain angle, so that the pulsed lasers may reflect back and forth inside the internal wall. In addition, the scanner may direct the pulses lasers towards the internal wall of the air duct along a horizontal line so that each area of the air duct may be scanned when the pulsed lasers are reflected back and forth inside the air duct, as further described below. In some embodiments, the scanner may have functions similar to those described for scan unit 112.

As further illustrated in FIGS. 4A and 4B, each of the fluid disinfection systems 400 and 450 may also be coated with a set of light reflectors (which may be also referred to as "laser reflectors") 412*a*/412*b* or 462*a*/462*b* along the internal wall(s) of the air duct 410 or 460. In some embodiments, the internal walls may be parallel to each other, and thus light reflectors 412*a*/412*b* or 462*a*/462*b* may be in parallel with each other. In some embodiments, the light reflectors 412*a*/412*b* or 462*a*/462*b* may be high reflectivity mirrors that include a layer of reflecting material on the surface. The reflecting material may have high reflectivity, e.g., over 95%. In one example, the coating reflecting material may be polished anodized aluminum, mylar, silver, nickel, chromium, etc. It is to be noted that while two light reflectors are illustrated for each fluid disinfection system 400 or 450, in some embodiments, the light reflector(s) may be a single circular piece, a single elliptical piece, or may be three pieces, four pieces, five pieces, six pieces of mirrors, etc.

In some embodiments, in a specific disinfection process, laser emitter 406 or 456 may emit a series of pulsed lasers (e.g., DUV picosecond lasers) towards light reflectors 412*b* or 462*b* at a certain angle(s). Light reflectors 412*a*/412*b* or 462*a*/462*b* may continuously reflect the pulsed lasers back and forth (e.g., hundreds or thousands of times) until reaching the top of the air duct, thereby forming a light screen inside air duct 410 or 460. The formed light screen may have different shapes (e.g., rectangular, square, circle, polygon, ellipse, diamond, etc.), based on the configuration of the mirrors and air duct. As previously described, the formed light screen may cover each area inside the air duct under certain scan patterns. In some embodiments, when there is air or another fluid passing through the formed light screen, the virus or other pathogens 416*a* or 466*a* inside the air or fluid may be killed by the formed radicals as previously described, to become non-infectious particles 416*b* or 466*b* due to the damaged DNA/RNA. In this way, the air or another fluid passing through air duct 410 or 460 may get disinfected by the fluid disinfection systems 400 and 450. For instance, air duct 460 may be part of an air circulating system for a facility. The air inside the facility may be continuously disinfected by the fluid disinfection system 450 associated with air duct 460. For another instance, air duct 410 may be a part of a mobile air disinfection system that can also provide air disinfection or purification inside a facility, as further illustrated in FIG. 5.

Figure 5:
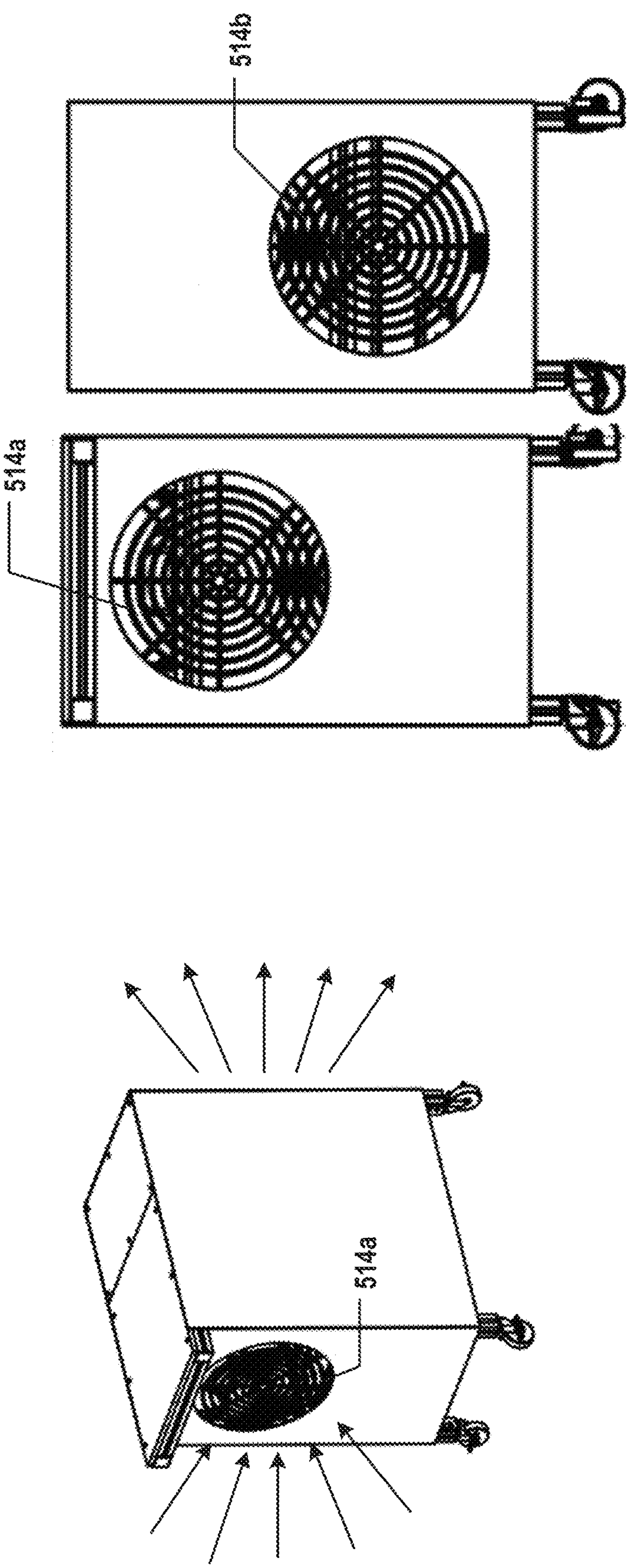
FIG. 5 illustrates various exemplary mobile fluid disinfection systems, according to various embodiments of the present disclosure.

FIG. 5 is a schematic diagram of an exemplary mobile air disinfection system 500, according to some embodiments of the disclosure. As illustrated in the figure, mobile air disinfection system 500 may include an air duct docketed inside a mobile station. The air duct may include an air inlet 514*a* and an air outlet 514*b*. Although not shown, mobile air disinfection system 500 may include a laser source for emitting pulsed lasers towards a part of the internal wall of the air duct inside system 500, similar to laser sources described in FIG. 4. The disclosed disinfection system 500 may be applied to a relatively closed facility, such as a room, like an air purifier. That is, air may be continuously circulated through the mobile air disinfection system 500, so as to continuously disinfect the air inside the facility. Due to its mobility, the disinfection system 500 may be applied to many different locations, thereby expanding its use in actual applications.

It is understood that mobile disinfection system 500 illustrated in FIG. 5 is just for illustrative purposes, but not for limitation. For instance, a mobile disinfection system 500 may be in a shape and/or size/scale different from those shown in FIG. 5. In addition, air inlet 514*a* and air outlet 514*b* can be in different positions of mobile disinfection system 500, and can be in different shapes or structures other than those shown in FIG. 5.

Figure 6A:
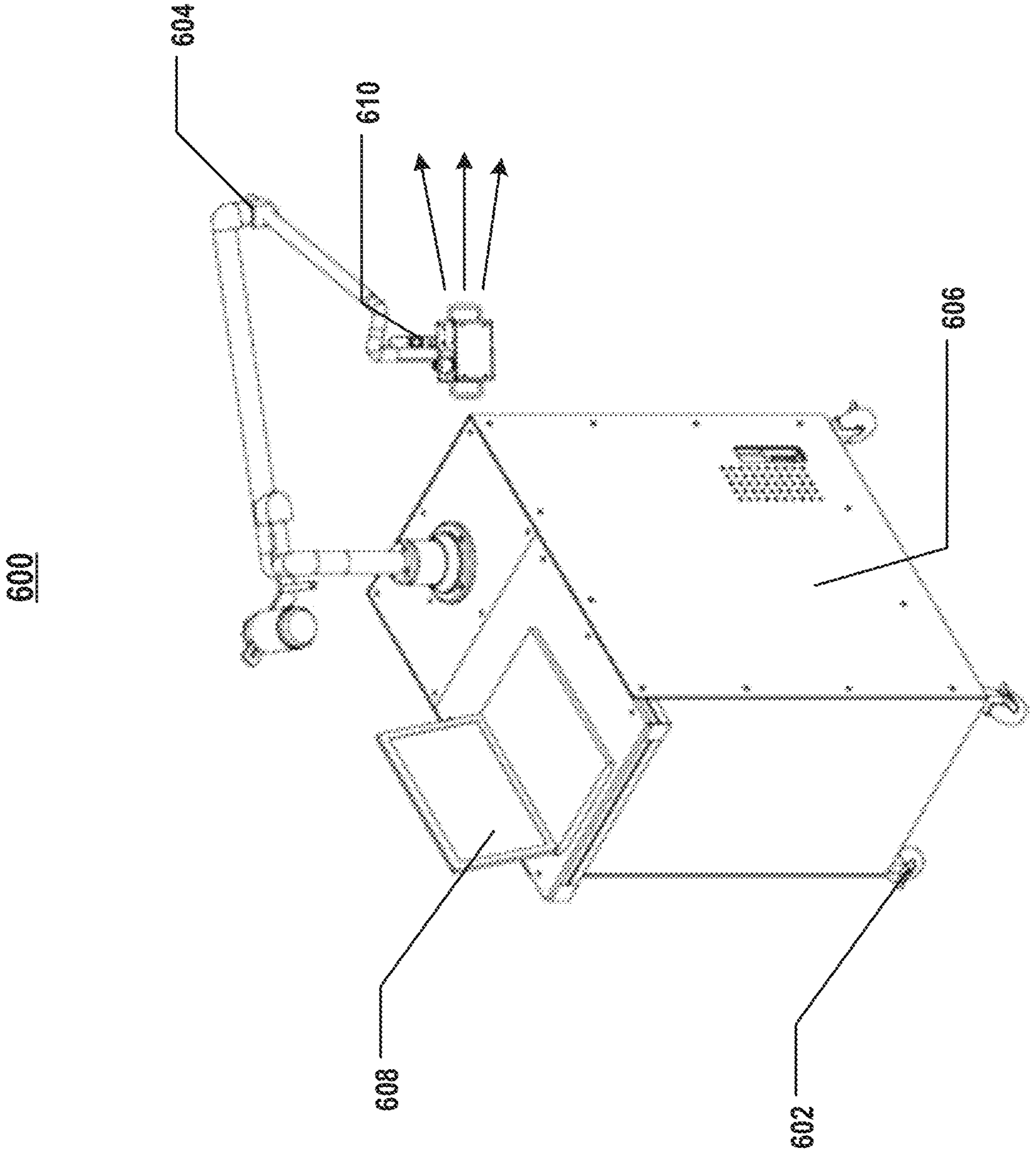
FIGS. 6A-6C illustrate schematic diagrams of exemplary structure surface disinfection systems with a movable arm, according to some embodiments of the present disclosure.
Figure 6B:
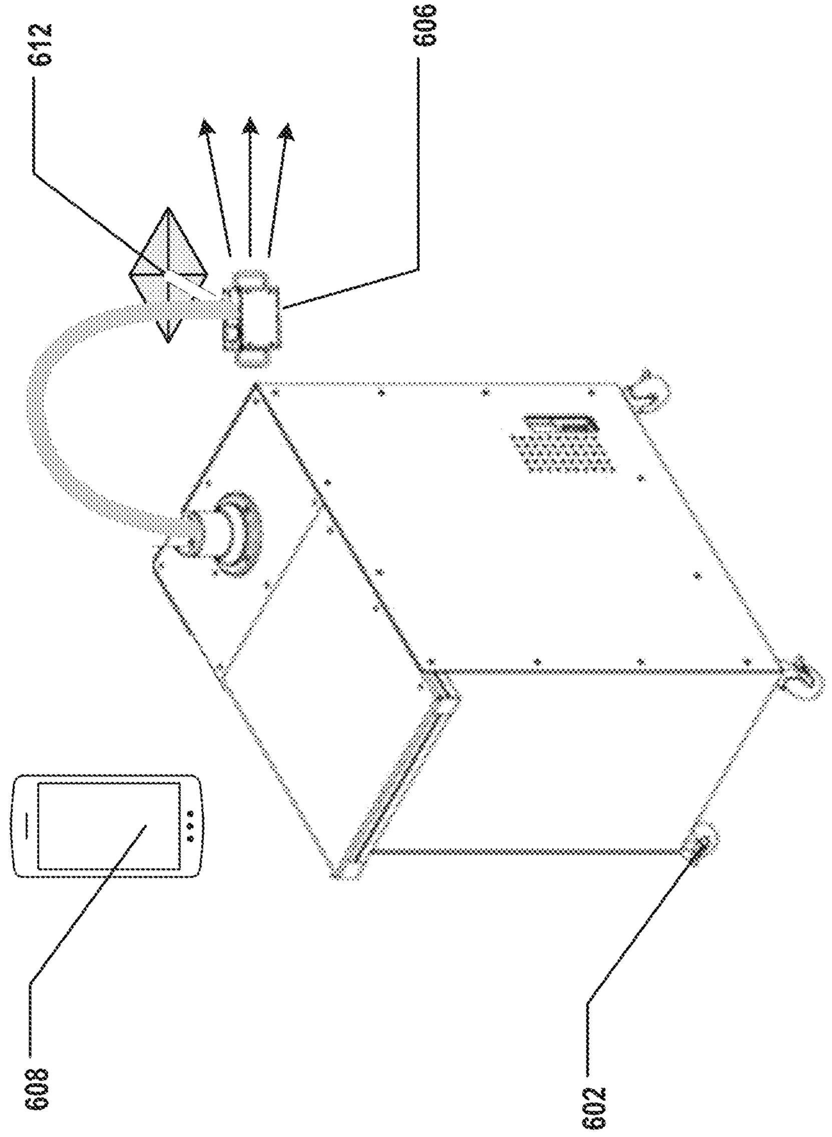
Figure 6C:
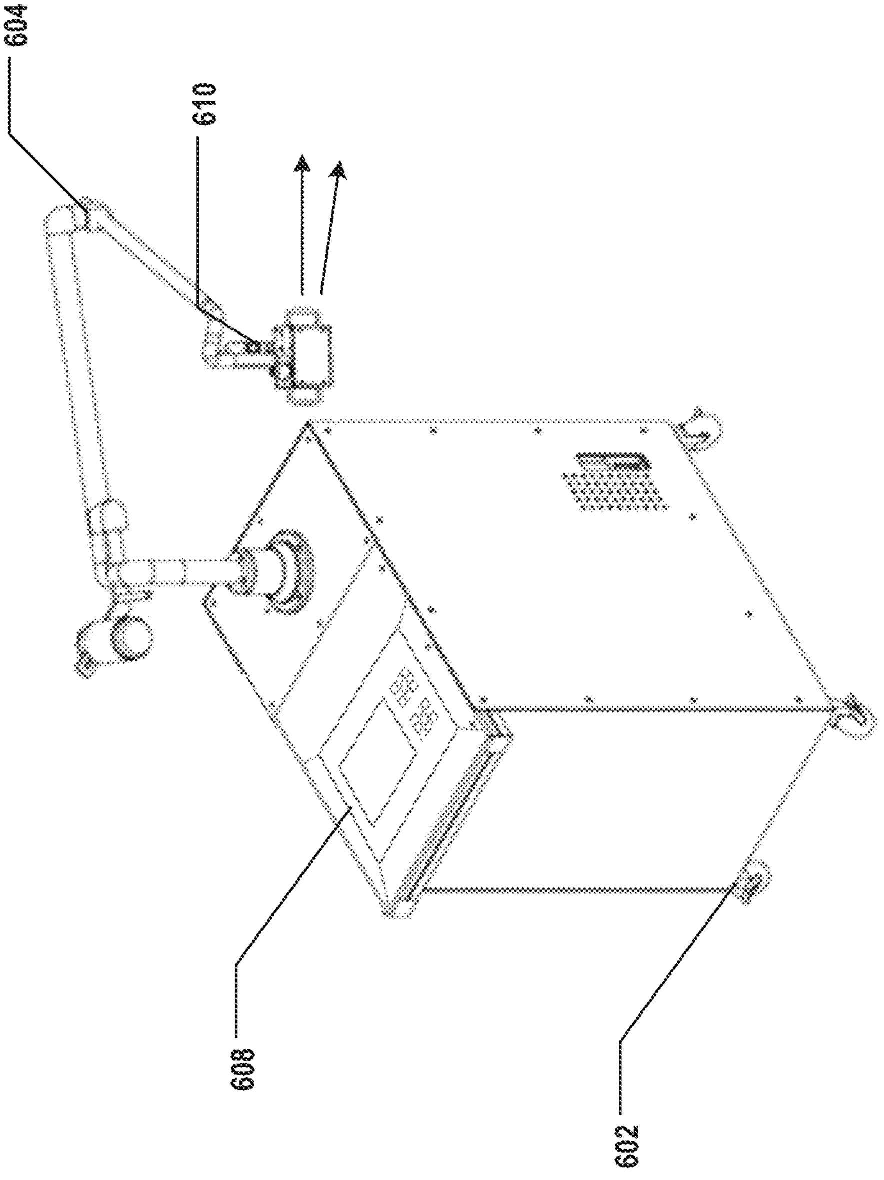

It is also understood that a disclosed DUV picosecond laser-based disinfection system is not limited to disinfection of air or other fluid passing through an air duct, but can be also used to disinfect the structure surface of an object. For instance, DUV picosecond lasers generated by a laser emitter may be directed directly towards object surfaces for disinfecting an object. To serve this purpose, a disinfection system may be equipped with an optical fiber or optical cable that is configured to transmit picosecond lasers emitted by a laser emitter within a short distance. The transmitted lasers may be directed towards object surfaces at one end (which may be referred to as "emitting end") of the optical fiber or optical cable. The optical fiber or optical cable may be aligned inside or along a fixed frame, or may be flexible in movement, depending on configurations. In addition, the emitting end of the optical fiber or optical cable may be held by a guiding apparatus for directing the emitted lasers towards different directions. Alternatively, the emitting end of the optical fiber or optical cable may be placed inside a handheld device that can be manipulated by an operator for surface disinfection. FIGS. 6A-6C illustrate schematic diagrams of exemplary mobile structure surface disinfection systems 600, according to some embodiments of the disclosure.

In FIG. 6A, a mobile structure surface disinfection system 600 may include a mobile station 602, a movable arm 604, a laser module 606, and a controlling system 608. Mobile station 602 may include rollers that drive the movement of mobile structure surface disinfection system 600. Movable arm 604 (which may be also referred to as "mobile arm") may include one or more arms that can be controlled to move optical fiber or optical cable inside the arm to different locations. Laser module 606 (not shown in detail in FIG. 6A) may emit pulsed lasers, e.g., picosecond DUV lasers, as previously described. The emitted lasers may be directed towards different object surfaces through a coupled optical fiber or optical cable inside movable arm 604. In some embodiments, mobile structure surface disinfection system 600 may further include a controlling system 608 that controls laser power of emitted lasers and controls the movement of movable arm 604. For instance, controlling system 608 may control laser module 606 to emit DUV picosecond lasers. For another instance, controlling system 608 may control movable arm 604 to move optical fiber or optical cable to target locations during a disinfection process. Controlling system 608 may be connected to movable arm 604 and laser module 606 through wired or wireless communication. It is to be noted that while optical fiber or optical cable is described as a tool for directing emitted lasers in movable arm 604, the present disclosure is not limited to such configurations. For instance, in one application, movable arm 604 may instead include a set of reflecting mirrors aligned along the inside surface of the movable arm, so as to transmit the emitted lasers towards different directions along the movable arm.

In some embodiments, controlling system 608 may additionally control the rotation of the emitting end of the movable arm. For instance, mobile structure surface disinfection system 600 may additionally include a gimbal or other kinds of adaptor 610 that may be controlled to rotate. By including such a gimbal or adaptor 610, controlling system 608 may also control the emitting end of the movable arm to rotate, so that emitted pulsed lasers can be directed towards different orientations. This may then allow mobile structure surface disinfection system 600 to disinfect structure surfaces from different angles, e.g., facing up when disinfecting the bottom surface of an object, facing down when disinfecting the top surface of an object, or facing left or right when disinfecting side surfaces of an object, etc. By controlling the location and/or rotation of the emitting end of the movable arm, objects with different shapes may be fully disinfected. In some embodiments, controlling system 608 may have the same functions as controller 108 as previously described.

FIG. 6B illustrates another mobile structure surface disinfection system 620, according to some embodiments of the disclosure. As can be seen, compared to FIG. 6A, there is no movable arm that controls the movement of the movable arm. Instead, the movement of the emitting end of the movable arm is controlled by a shift unit 612 that controls the emitting end to shift to different locations, as shown in FIG. 6B. In some embodiments, there is even no shift unit that controls the emitting end of the movable arm. Instead, the emitting end of the movable arm may be integrated into a handheld device, so that an operator may actually hold the device to point the emitting end of the movable arm towards object surfaces. In addition, controlling system 608 may be also different. For instance, in FIG. 6A, controlling system 608 may be a laptop computer or may be in a form of an application running on a laptop computer. On the other hand, in FIG. 6B, controlling system 608 may be a mobile device (e.g., a cell phone or a tablet) or may be in a form of an application running on such a mobile device. Although not shown, the disclosed disinfection system 620 may also include a laser module configured to emit DUV picosecond lasers for surface disinfection, as described in FIG. 6A.

FIG. 6C illustrates yet another mobile structure surface disinfection system 640, according to some embodiments of the disclosure. As can be seen, compared to FIGS. 6A and 6B, controlling system 608 may be in a different form again. For instance, controlling system 608 may be in the form of a monitor device integrated into mobile station 602. The monitor device may be connected to laser module 606, movable arm 604, and/or gimbal/adaptor 610 in a wired or wireless manner.

As can be seen, different apparatuses may be used for guiding lasers towards object surfaces. In addition, control units for controlling the operation of disinfection systems may also vary and exist in different forms. In some embodiments, a mobile station may be not movable and may be in any form that can hold a laser mobile and relevant elements for the disclosed disinfection system. In other words, the disclosed disinfection system may be in many different forms or configurations, as long as the emitted DUV picosecond lasers are able to be directed towards object surfaces for disinfection.

Referring now to FIG. 7, a flowchart of an exemplary method 700 for fluid or structure surface disinfection using picosecond DUV laser is provided. It is to be noted that the operations shown in method 700 are not exhaustive and that other operations may be performed as well before, after, or between any of the illustrated operations. Further, some of the operations may be performed simultaneously, or in a different order than that shown in FIG. 7.

Referring to FIG. 7, method 700 starts at operation 702, in which a series of pulsed lasers are generated. In some embodiments, the series of pulsed lasers are picosecond DUV lasers. For instance, the pulsed lasers may have a duration between 1 picosecond and some tens of picoseconds, between 50 femtoseconds and 50 picoseconds, etc. In other words, the pulsed lasers are ultrafast lasers or ultrashort pulse lasers. In some embodiments, each of the pulsed lasers includes a series of bursts. In some embodiments, operation 702 may be implemented by laser source 102 of disinfection system 100, a laser module of disinfection system 400, 450, 500, or 600.

Method 700 then proceeds to operation 704 or 708, as illustrated in FIG. 7, in which the generated series of pulsed lasers may be directed towards a portion of an internal surface of a structure (e.g., an air duct internal wall) in operation 704 or a portion of an external surface of a structure (e.g., a target object surface) in operation 708.

In operation 704, when directing the generated series of pulsed lasers towards the internal structure, the pulsed lasers may be directed towards the internal wall at a certain angle. The mirror(s) on the internal wall of the air duct may continuously reflect the pulsed lasers back and forth inside the air duct, thereby forming a light screen. In this way, when air or another fluid passes through the air duct, the virus or other possible pathogens within the air or fluid may be killed by the light screen formed by the reflecting picosecond DUV lasers.

In operation 706, the generated series of pulsed lasers may form a predefined shape by the mirrors inside the air duct. In some embodiments, depending on the configuration of the internal structure of the air duct (e.g., depending on the shape of the mirrors or air duct shapes), the formed light screen may have a specific shape. For instance, the formed light screen may be in a shape of a rectangle, a square, a circle, a diamond, an ellipse, etc. In some embodiments, the formed shape of the light screen may match the shape of the internal structure of the air duct in at least one dimension (e.g., in a dimension perpendicular to the flowing direction of the fluid inside the air duct), so as to ensure that no air pass through the air duct without being through a light treatment during a disinfection process. This may ensure that air or other fluids be fully disinfected by the formed light screen.

As previously described, in some embodiments, the pulsed lasers may be directed towards a portion of an external surface of a structure (e.g., an object). Accordingly, in operation 708, the generated series of pulsed lasers may be directed towards a structure surface. In some embodiments, the pulsed lasers may be directed towards the structure surface within a certain distance for effective disinfection. In some embodiments, to make sure disinfection of the whole surface of the object, the laser source or laser module may be movable (e.g., through the movable arm) so that different areas of the structure surface may be disinfected by the pulsed lasers. As previously described in FIG. 1, disinfection system 100 may include a detection module 110 (e.g., a sensor or a camera) to capture the surface structure of an object, so that the exact area to be disinfected may be monitored in real time in a disinfection process. As also described in FIG. 1, disinfection system 100 may additionally include a controller 108 to control the movement and/or rotation of the laser module or laser source. The controller may control the movement and/or rotation of the laser module or laser source based on the surface structure of the object. For instance, based on the information obtained by the detection module, the controller may control the movement and/or rotation of the laser source or laser module. This may ensure the whole external surface of an object to be light-treated or disinfected.

Method 700 then proceeds to operation 710, in which the disinfection effect of air or other fluids in the air duct or the external surface of an object may be monitored. In some embodiments, the disinfection effect may be monitored through infection studies, or through proper approaches. For example, by comparing samples (e.g., air samples or samples collected from an external surface of an object) before and after disinfection, the disinfection efficiency may be obtained.

Method 700 then proceeds to operation 712, to determine whether to adjust the power of the generated pulsed lasers based on the disinfection effect. In some embodiments, an efficiency threshold may be predefined and used to determine whether to adjust the power of the generated pulsed lasers. In one example, the efficiency threshold may be set to 90% (i.e., 90% of the virus is killed), 95%, 98%, or another proper value. When the obtained disinfection efficiency is less than this value, it may be determined to adjust (e.g., increase) the laser power of the generated pulsed lasers.

Method 700 then proceeds to operation 714, to adjust the laser power for generating the series of pulsed lasers. In some embodiments, different strategies may be applied to adjust the laser power in generating the series of pulsed lasers. In one example, the laser power may be adjusted to different levels. For instance, the laser source or laser module may be set to have a number of power levels (e.g., five levels, seven levels, nine levels, etc.) with different laser powers (e.g., peak power). To adjust the laser power means to adjust to a different level (e.g., increase from level 3 to level 5), so as to adjust the laser power for the generated series of pulsed lasers. In another example, the laser power may be set to be continuously adjustable instead of a level-by-level adjustment. For instance, the laser power may be adjustable to any value within a laser power range (e.g., any value between peak power of 10 MW to 50 MW).

In some embodiments, the laser power of the laser source or laser module in a disinfection system may be adjusted based on other factors. For instance, the laser power of the laser source or laser module may be adjusted based on the air flow rate of the disinfection system. For instance, when the air/fluid flows into/out of the air duct in a fluid disinfection system increases or decreases, the laser power may increase or decrease accordingly, even without requiring determining the disinfection efficiency.

In some embodiments, after the laser power is adjusted through operation 714, method 700 may return to operation 702 from operation 714, to allow the laser module or laser source to emit pulsed lasers with the adjusted laser power. In some embodiments, if it is determined not to adjust the power of the generated pulsed lasers based on the disinfection effect, method 700 may proceed from operation 712 to operation 702, to continue to generate a series of pulsed lasers using the same laser power as previously used. The disinfection process may be then continuously conducted using the same laser power without adjusting the laser power.

Although not shown, in some embodiments, scan patterns may also be adjusted or updated through another process (not shown). The scan pattern may be adjusted or updated based on the detection of the object structure as previously described. In some embodiments, additional parameters besides laser power and scan pattern may also be adjusted, so as to optimize the performance of a disinfection system, to promote its application in minimizing the impact of the pandemic of COVID 19 or another virus.

Another aspect of the disclosure is directed to a non-transitory computer-readable medium storing instructions which, when executed, cause one or more processors to perform the methods, as discussed above. The computer-readable medium may include volatile or non-volatile, magnetic, semiconductor, tape, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

The foregoing description of the specific embodiments will so reveal the general nature of the present disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Embodiments of the present disclosure have been described above with the aid of functional building blocks illustrating the implementation of specified functions and relationships thereof. The boundaries of these functional building blocks have been arbitrarily defined herein for the convenience of the description. Alternate boundaries may be defined so long as the specified functions and relationships thereof are appropriately performed.

The Summary and Abstract sections may set forth one or more but not all exemplary embodiments of the present disclosure as contemplated by the inventor(s), and thus, are not intended to limit the present disclosure and the appended claims in any way.

The breadth and scope of the present disclosure should not be limited by any of the above-described exemplary embodiments, but should be defined only in accordance with the following claims and their equivalents.

What is claimed is:

1. A system for fluid or structure surface disinfection, comprising:
- a laser source configured to generate a laser stream;
- a detection module configured to detect shape and size of a portion of a surface of a structure;
- an optical module configured to shape the laser stream, direct the laser stream toward the portion of the surface of the structure, and generate a series of focused laser spots on a target object under disinfection; and
- a controller coupled to the optical module and configured to:
  - control the optical module to direct the laser stream toward the portion of the surface of the structure; and
  - determine a disinfection efficiency based on a disinfection effect of the target object, compare the disinfection efficiency with a predefined efficiency threshold, and, in response to the disinfection efficiency being less than the predefined efficiency threshold, increase a power of the laser stream and adjust a degree of overlapping between adjacent focused laser spots on the target object under disinfection.

2. The system of claim 1, wherein the laser stream is a series of pulsed lasers, and each of the pulsed lasers comprises a series of bursts.

3. The system of claim 1, wherein the structure is an air duct, and the surface of the structure is an internal wall of the air duct, wherein the internal wall of the air duct comprises a first side and a second side opposite to the first side.

4. The system of claim 3, wherein each of the first side and the second side of the internal wall is coated with a laser reflector.

5. The system of claim 4, wherein the laser reflector on the first side and the laser reflector on the second side are in parallel with each other.

6. The system of claim 5, wherein the laser reflector is a high reflectivity mirror.

7. The system of claim 2, wherein the optical module comprises a focus unit configured to focus each of the pulsed lasers such that a dimension of a focused laser spot on the surface of the structure is between 1 micrometer (μm) and 500 μm.

8. The system of claim 7, wherein the focus unit is further configured to control the pulsed lasers to allow the focused laser spot on the surface of the structure to have a predefined shape.

9. The system of claim 2, wherein the optical module comprises a scan unit configured to, based on a control of the controller, change a direction in which the pulsed lasers emit to the portion of the surface of the structure.

10. The system of claim 9, wherein, to change the direction of the pulsed lasers, the scan unit is configured to emit the pulsed lasers to the surface of the structure at a predefined angle.

11. The system of claim 9, wherein, to change the direction of the pulsed lasers, the scan unit is configured to emit the pulsed lasers to the surface of the structure according to a predefined pattern.

12. The system of claim 2, wherein the controller is further configured to adjust a power of the generated laser stream.

13. The system of claim 1, further comprising a mobile arm configured to hold the laser source to allow the laser source to move to a predefined location and orientation with respect to the surface of the structure.

14. The system of claim 2, wherein a duration of each of the pulsed lasers is not greater than 50 picoseconds.

15. The system of claim 14, wherein the duration of each of the pulsed lasers is between 50 femtoseconds and 50 picoseconds.

16. The system of claim 8, wherein the predefined shape is one of a circle, a rectangular, an ellipse, a polygon, and a diamond.

17. The system of claim 12, wherein, to adjust the power of the generated laser stream, the controller is further coupled to the laser source and configured to control the laser source to adjust at least one of a power of the laser source and a number of bursts in each of the pulsed lasers.

18. The system of claim 1, wherein the laser source is configured to generate a laser in a wavelength range of 200-300 nm.

* * * * *